United States Patent [19]

Knell

[11] 4,058,573
[45] Nov. 15, 1977

[54] PROCESS FOR THE ADDITION OF GASEOUS NON-HALOGENATED OLEFINS AND ACETYLENES TO PERFLUOROALKYL IODIDES

[75] Inventor: Martin Knell, Ossining, N.Y.

[73] Assignee: Ciba-Geigy Corporation, Ardsley, N.Y.

[21] Appl. No.: 457,879

[22] Filed: Apr. 4, 1974

Related U.S. Application Data

[63] Continuation of Ser. No. 159,515, July 2, 1971, abandoned, which is a continuation-in-part of Ser. No. 4,179, Jan. 14, 1970, abandoned, which is a continuation-in-part of Ser. No. 693,148, Dec. 26, 1967, abandoned.

[51] Int. Cl.$^2$ .............................................. C07C 21/20
[52] U.S. Cl. .......................... 260/653.1 T; 260/653; 260/653.3
[58] Field of Search ............... 260/653, 653.1 T, 653.3

[56] References Cited

U.S. PATENT DOCUMENTS

| | | | |
|---|---|---|---|
| 3,145,222 | 8/1964 | Brace | 260/653 |
| 3,226,449 | 12/1965 | Blanchard et al. | 260/653.1 T |
| 3,337,435 | 8/1967 | Haszeldine | 260/653.3 |

OTHER PUBLICATIONS

Lovelace et al., Aliphatic Fluorine Compounds, pp. 39 and 40, (1958).

*Primary Examiner*—C. Davis
*Attorney, Agent, or Firm*—Karl F. Jorda; Edward McC. Roberts; Prabodh I. Almaula

[57] ABSTRACT

Liquid perfluoroalkyl iodides are added to non-halogenated gaseous olefins or non-halogenated acetylenes in the presence of free radical generating catalysts to produce an additive reaction product essentially free of telomers. The gaseous olefin or acetylene is bubbled through liquid perfluoroalkyl iodide and catalyst at temperatures of 40° to 220° C and pressures no higher than atmosphere. Illustratively, ethylene is added to 1-iodoperfluoroheptane in the presence of benzoyl peroxide.

14 Claims, No Drawings

PROCESS FOR THE ADDITION OF GASEOUS NON-HALOGENATED OLEFINS AND ACETYLENES TO PERFLUOROALKYL IODIDES

RELATED APPLICATIONS

This invention is a continuation of Ser. No. 159,515 filed July 2, 1971, now abandoned, which is a continuation-in-part of Ser. No. 4,179 filed Jan. 14, 1970, now abandoned, which application in turn is a continuation of Ser. No. 693,148 filed Dec. 26, 1967 and now abandoned. Filed concurrently with Ser. No. 159,515 were two other continuations-in-part of Ser. No. 4,179 entitled Process for the Addition of Perfluoroalkyl Iodides to Gaseous Halogenated Olefins, Ser. No. 159,513, now abandoned, and Process for the Addition of Gaseous Olefins and Acetylenes to Iodo Fluorinated Ethers, Ser. No. 159,514, now abandoned.

BACKGROUND OF THE INVENTION

This invention relates to an improved process for the addition of liquid perfluoroalkyl iodides to non-halogenated hydrocarbon olefins and non-halogenated hydrocarbon acetylenes. The present invention may be considered to be in a related area of technology as two prior art patents, namely, Brace U.S. Pat. Nos. 3,145,222 and Blanchard et al 3,226,449.

Brace U.S. Pat. No. 3,145,222 discloses perfluoroalkyl iodides can be added to olefins or acetylenes in the presence of free-radical generating catalysts in acceptable conversions and yields. The same reactant materials are disclosed in the present invention. The process of Brace is carried out at temperatures ranging from about 50° to about 190° C, depending primarily upon the specific free-radical generating catalyst that is employed. If the olefin or acetylene employed is a gas at reaction temperature and atmospheric pressure, then a superatmospheric pressure system must be employed in the practice of the Brace process. This naturally adversely affects the economic feasibility of the process because of the expensive pressure equipment necessary to maintain the conditions and the complication involved thereby. Thus, for example, in order to adjust the concentration of the reactants, the pressure must be adjusted. Safety in operation is also sacrificed by the necessity of working with flammable gas under pressure.

Another teaching in the prior art for obtaining perfluoroalkyl iodide addition products is by a process disclosed in Blanchard et al, U.S. Pat. No. 3,226,449. The patentees disclosed telomerization of perfluoroalkyl iodides with tetrafluoroethylene to obtain higher perfluoroalkyl iodides in the presence of a free radical generating catalyst. This process sets forth injecting tetrafluoroethylene and a free radical generating catalyst during a reaction cycle into liquid perfluoroethyl iodide and mixtures thereof with n-perfluorobutyl iodide which liquid also contains the catalyst in a pressure vessel maintained at a pressure between 225 psi to 700 psi at a temperature of 80° to 170° C. The reaction mixture products are of the structure $F(CF_2)_mI$ where m is an even integer from 6 to 12.

The process disclosed by Blanchard et al represents a contribution to the art. However, several inherent limitations exist, namely:

1. Process is limited to a narrow edge of source materials.

2. Process is limited to relatively high pressure conditions involving expensive equipment and inherent hazardous reaction conditions.

3. Process is limited to production of telomers.

In contrast to the prior art teachings, the present process overcomes inherent limitations by its novel aspects and, more specifically, overcomes important disadvantages present in the teachings of Brace et al and Blanchard et al.

It is an object of the present invention to produce a reactant addition product of perfluoroalkyl iodides and gaseous non-halogenated olefins and/or acetylenes which product is formed at or below atmospheric pressure.

It is a further object of the present invention to produce a reactant addition product of perfluoroalkyl iodides and gaseous non-halogenated olefins or acetylenes which reaction product is essentially free of telomers.

SUMMARY OF THE INVENTION

An improved process is disclosed for the addition of perfluoroalkyl iodides of the formula:

$$ZC_nF_{2n}I$$ 

wherein Z represents F or I, n is an integer of 4 – 18, preferably 6 – 10, in which the perfluoro group may be straight or branched chained with non-halogenated olefins or acetylenes.

The starting gaseous non-halogenated hydrocarbon olefins and/or acetylenes preferably are ethylene or acetylene or various substituted members of each series.

The starting perfluoroalkyl iodide may consist of a mixture of several perfluoroalkyl iodides.

The present process produces a final end product which is essentially free of telomers regardless of the mole ratios of starting materials of liquid perfluoroalkyl iodides and gaseous non-halogenated olefins and non-halogenated acetylenes. The perfluoroalkyl iodide will add to the olefin or acetylene to form a 1:1 adduct when Z represents F or form a 1:2 adduct when Z represents I.

The technique employed herein is carried out either at atmospheric pressure or under vacuum conditions. Most preferably, the reaction is at atmospheric pressure bypassing use of expensive equipment.

The process comprises bubbling a gaseous non-halogenated olefin, acetylene or mixutres thereof into the perfluoroalkyl iodide maintained at a temperature between 40° to 220° C, and in the presence of a free radical generating catalyst such as benzoyl peroxide.

DETAILED DESCRIPTION OF THE INVENTION

Employing the reactant material of a liquid perfluoroalkyl iodide and a gaseous non-halogenated olefin or non-halogenated acetylene under the reactant conditions disclosed herein, a product with absence of telomers may be made over a wide range of process variables including varying ratios of olefin or acetylene to perfluoroalkyl iodide.

As disclosed, perfluoroalkyl iodide employed herein is of the following formula:

$$ZC_nF_{2n}I \qquad (I)$$ 

wherein Z represents F or I, n is an integer from 4 to 14 – 18 and more preferably 6 to 10. The perfluoro group may be straight or branch chained, although more desirably from the utility standpoint, the perfluoro group is a straight chain.

The other reactant material is a gaseous non-halogenated hydrocarbon olefin or acetylene such as ethylene or acetylene and the various substituted members of each series. Substitution may be by alkyl groups containing illustratively 1 to 4 carbon atoms and most preferably, 1 – 2 carbon atoms.

In order to initiate the reaction, a necessary component is a free radical generating catalyst such as the type employed by Brace in U.S. Pat. No. 3,145,222. Typical of these free radical generators are 2,2'-azobisisobutyronitrile, acyl peroxides, di-tert-butyl peroxide and benzoyl peroxide.

To illustrate the resulting addition when Z represents F, the following products will be formed dependent upon whether an olefin or acetylene is employed:

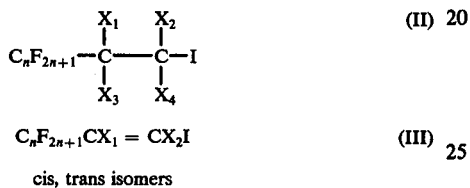

$$C_nF_{2n+1}CX_1 = CX_2I \quad \text{(III)}$$

cis, trans isomers

In the above formulas $X_1$, $X_2$, $X_3$ and $X_4$ represent an alkyl of 1 to 4 carbon atoms or hydrogen. Most desirably $X_1$, $X_2$, $X_3$ and $X_4$ will represent at most two alkyl groups. In other words concerning Formula III, it is desirable that two or more atoms of hydrogen be present.

In similar fashion when Z represents I, a further addition with either the olefin or acetylene will also take place adjacent to the second iodine atom.

A requirement in this process is the non-halogenated olefin or acetylene be gaseous under the operating conditions while the perfluoroalkyl iodide be liquid at the reacting temperature. Generally, operating temperatures of 40°–50° to 220° C are suitable, although temperatures below 100° C are more desirable. It is most preferable that atmospheric pressure conditions be employed with the perfluoroalkyl iodide liquid and thus pressurized equipment is totally unnecessary. While use of partial vacuum conditions obtains similar reactant results, such operating conditions are less desirable from the standpoint of increased equipment costs.

As disclosed previously, the reactant materials and reactant conditions produce an addition product that is considered free of telomers. However, for the purpose of accuracy, the reactant product may be considered to be "essentially free of telomers." As defined herein, "essentially free of " is employed to mean that trace quantities of telomers could possibly be detected in the reaction mixture. However, for all practical purposes, the reactant product does not contain telomers. The addition of the perfluoroalkyl iodide to the olefin or acetylene will form a 1:1 adduct when Z represents F and a 1:2 adduct when Z represents I. Therefore in the present context the absence of telomeric products refers to the absence of the addition product as other than 1:1 adduct or 1:2 adduct when Z of Formula I represents F and I respectively. Illustratively when the final compound is of the formula $C_nF_{2n+1}(CX_1X_3CX_2X_4)_nI$, $n$ will only represent 1.

The absence of telomeric products is obtained over a broad range of operating conditions. Absence of telomerization is obtained and the process is considered to be insensitive to operating conditions such as the rate of introduction of the gaseous non-halogenated olefin or acetylene into the perfluoroalkyl iodide or the employed mole ratios of each reactant. The present process allows fluctuation in operating condition parameters into producing the desired reactant product.

The process of addition of perfluoroalkyl iodide to an olefin is considered to comprise several steps, each of which must take place with high efficiency if a chain reaction is to be sustained. These steps may be described as follows:

1. Initiator decomposition: $(RCOO)_2 \rightarrow 2R\bullet + 2CO_2$
2. Radical displacement: $R\bullet + R_FI \rightarrow R_F\bullet + RI$
3. Initiation: $R_F\bullet + CX_1X_2 = CX_3X_4 \rightarrow R_FCX_1X_2CX_3X_4\bullet$
4. Transfer (1): $R_FCX_1X_2CX_3X_4\bullet + R_FI \xrightarrow{k_t} R_FCX_1X_2CX_3X_4I + R_F\bullet$
5. Propagation: $R_FCX_1X_2CX_3X_4\bullet + CX_1X_2 = CX_3X_4 \xrightarrow{k_p} R_F(CX_1X_2\text{-}CX_3X_4)_2\bullet$
6. Transfer (2): $R_F(CX_1X_2CX_3X_4)_2\bullet + R_FI \rightarrow R_F(CX_1X_2CX_3X_4)_2I + R_F\bullet$ The relative size of rate constants $k_p$ and $k_p$ (eq. 4 and 5) determines in part the extent of chain growth which occurs before the stable final products are formed (eq. 4 and eq. 6).

The concentration of olefin and $R_FI$ (telogen) also exert a significant influence on the ratio of products; a high concentration of olefin, as with ethylene under pressure, generally leads to a mixture of products $R_F(CH_2CH_2)_nI$, ($n = 1, 2, 3$ and higher.) The efficiency of the chain reaction, however, suffers if the olefin concentration is too low for initiation of the chain to begin (eq. 3). Side-reactions become significant if the chain reaction is not sustained. Such processes as hydrogen abstraction, coupling of radicals and radical-trapping reactions with oxygen, for example, are observed.

7. $R_F\bullet + RH \rightarrow R_FH + R\bullet$
8. $R_F\bullet + R_F\bullet \rightarrow R_FR_F$ These reactions are obviously undesirable, as the chain sequence is broken and the valuable starting materials are wasted. Hence, it is most unusual that an efficient, high yield free radical chain reaction of a reactive telogen such as a perfluoroalkyl iodide with an olefin such as ethylene or propylene, be obtained under conditions during which only a very low concentration of gaseous olefin is present. The solubility of a gaseous substance such as ethylene (bp-103° C) in a perfluoroalkyl iodide at, for example 100° C, is considered to be practically negligible. In fact, in the absence of a free radical chain reaction, absorption of ethylene, for example, in a liquid perfluoroalkyl iodide does not occur to an observable extent. It is considered prior to this disclosure that gaseous olefins would be employed under pressure, to bring about free radical reactions of the type being discussed.

Generally, the flow of gaseous non-halogenated olefin or acetylene is into the bottom of the reaction mixture of perfluoroalkyl iodide and free radical generating catalyst, and for maximum efficiency is preferably adjusted to a slight excess over the rate of reaction. However, a variance in flow ratios to yield a product free of telomers may be utilized.

The substantial completion of the reaction is indicated when the rate of absorption of the non-halogenated olefin or acetylene has practically ceased.

Following completion of the reaction, the product is purifed by vacuum distillation.

High rates of addition are possible based upon the initial perfluoroalkyl iodide starting material. Conversions of 98% have been obtained.

Simply, the process requires bubbling the gaseous non-halogenated olefins, acetylene or mixtures through the liquid reaction mixture of free-radical generating catalyst and liquid perfluoroalkyl iodide maintained at atmospheric pressure within the operating temperature of 40°-50° to 220° C. The reaction temperature within the disclosed range is determined in part by the type of catalyst employed so that free radical generation occurs. Also, the liquid perfluoroalkyl iodide need not be a liquid over the entire temperature range disclosed, but will be a liquid under the chosen operating temperature within the range of 40° to 220° C.

Reaction times may be varied within wide limits and generally times of 1 to about 20 hours are suitable. In most instances, a period of about 2 hours to about 10 hours is preferred. Two hours is generally sufficient to allow a major portion of the starting perfluoroalkyl iodide to be consumed and practically, 3 - 4 hours may bring substantial reaction completion.

A broad range of free radical generating catalysts are operable and desirable in the present disclosure such as those disclosed by Brace in U.S. Pat. No. 3,145,222. Generally speaking, amounts of catalyst of 0.001 to 0.1 mol per mol of perfluoroalkyl iodide are satisfactory with about 0.05 mol generally preferred. Greater amounts of catalyst could be employed but no significant advantage is realized.

Generally speaking, a wide variety of catalysts initiate the chemical addition. Suitable examples are disclosed in Brace U.S. Pat. No. 3,145,222. However, from the standpoint of optimum usage, criticality in catalyst does exist. With an efficient catalyst the rate of reaction is increased, thereby obtaining the maximum product yield in a relatively short period of time. With an inefficient catalyst, greater time periods are necessary, additional quantities of gaseous reactants are utilized, and/or more catalyst is required. Desirable catalysts include aromatic acyl peroxides, such as benzoyl peroxides, alkyl peroxides, such as di-tert-butyl peroxide, and aliphatic-acyl peroxides, such as dilauroyl peroxide. An example of a catalyst giving slow rates of reaction is an azo catalyst such as azobis-isobutyronitrile.

Compounds obtained by the process of this invention are useful intermediates in the production of many products which possess valuable surface active properties. Products with such surface active properties, for example, have found wide use as components of textile finishes which impart oil and/or water repellent qualities to textile fabric impregnated with such finishes. Other examples of utility include use for the preparation of alcohols (U.S. Pat. No. 3,283,012), of methacrylate esters (U.S. Pat. No. 3,239,557), of amines, $C_nF_{2n+1}(CH_2)_aN(R)Z$ (Fr. Pat. No. 1,532,284), nitriles, $C_nF_{2n+1}CH_2CH_2CN$ (Fr. Pat. No. 1,560,544) and malonic esters, $R_fCH_2CH_2CH(COOR)_2$ and $(R_fCH_2CH_2)_2C(COOR)_2$ (U.S. Pat. No. 3,478,116).

While the process is primarily intended to be carried out at normal atmospheric pressure, it is, of course, apparent that pressures less then atmospheric may likewise be employed within the teaching of the invention provided, however, it requires that the perfluoroalkyl iodide remain liquid at such lesser pressure. The complexity of the equipment required, pressure control and the like, make this alternative less desirable than operation under normal atmospheric pressure conditions.

In the following examples, parts are by weight and the relationship between parts by weight and parts by volume is as that of grams to cubic centimeters, unless otherwise indicated:

EXAMPLE 1

A 200 ml pear-shaped flask is fitted with thermometer, gas inlet tube, and condenser. The flask is charged with 100 parts of 1-iodoperfluoroheptane and one part of benzoyl peroxide and brought to 80° - 5° C before addition of ethylene. Ethylene is bubbled through the mixture for about 10.5 hours at which time the ethylene absorption has slowed to a point indicating substantial completion of the reaction. The reaction mixture is then allowed to cool to room temperature and at room temperature the reaction mixture is a solid. VPC discloses no starting material and only one product peak. The crude yield is essentially quantitative.

Distillation yields 1,1,2,2-tetrahydro-1-iodoperfluorononane free of telomers B.P. 89° - 90° C at 23mm pressure, M.P. 40° - 45° C. (88.5% recovery).

Analysis for $C_7H_4F_{15}I$

Calculated — C, 20.67; H, 0.77; F, 54.39. Found — C, 20.14; H, 0.71; F, 53.37.

EXAMPLE 2

A mixture of 10 parts of 1-iodoperfluoroheptane and one part benzoyl peroxide in a 25 ml pear-shaped flask, fitted with a condenser and gas inlet tube, is heated to 95° C. Propylene is bubbled into the mixture for about 2 hours, after which time the absorption of propylene slows down and stops. VPC indicates that there is no perfluoroalkyl iodide remaining and the desired product is present. The reaction mixture is then filtered to remove a small amount of insoluble material which is a by-product of the reaction with the catalyst, and then the filtrate is distilled at 13 mm pressure. 8.44 parts of 1,1,1,2,3,3-hexahydro-2-iodoperfluorodecane free of telomers boiling at 119° - 120° C are obtained. NMR spectrum confirms the desired structure.

Analysis for $C_{10}H_6F_{15}I$

Calculated — C, 22.32; H, 1.12; F, 52.97. Found — C, 22.49; H, 1.17; F, 52.40.

EXAMPLE 3

10 parts of 1-iodoperfluoroheptane and 0.1 part of benzoyl peroxide are placed in a 25 ml pear-shaped flask as in the foregoing example. The reaction mixture is heated to 95° C and isobutylene is bubbled through the mixture for about 2 hours after which the absorption slows down and stops. VPC indicates only a minor proportion of the 1-iodoperfluoroheptane remaining. The mixture is distilled at 4.5 mm pressure. 9.17 grams of 1,1-dimethyl-2,2-dihydro-1-iodoperfluorononane free of telomers boiling at 82° - 84° C are obtained.

Analysis for $C_{11}H_6F_{15}I$

Calculated — C, 23.93; H, 1.46; F, 51.62 Found — C, 24.02; H, 1.48; F, 51.74

EXAMPLE 4

A mixture of 10 parts of 1-iodoperfluoroheptane and 0.1 part of benzoyl peroxide in a 25 ml pear-shaped flask is heated at 90° - 95° C while trans butene-2 is bubbled into the reaction mixture. Addition of the olefin is continued until VPC indicates that all the perfluoroheptyl iodide has been converted. The reaction product is then distilled at 4.5 mm pressure giving 7.55 parts of 1,2-dimethyl-1,2-dihydro-1-iodoperfluorononane boiling at 86° – 90° C. VPC shows two peaks indicating that a mixture of the diastereoisomers of 1,2-dimethyl-1,2-dihydro-1-iodoperfluorononane is obtained, which mixture is free of telomers.

Analysis for $C_{11}H_8F_{15}I$

Calculated — C, 23.93; H, 1.46; F, 51.62. Found — C, 24.27; H, 1.58; F, 52.19.

EXAMPLE 5

The above procedure of Example 4 is repeated only using cis butene-2 instead of the trans isomer. After the reaction is over, the product is distilled at 88° – 90° C at 4.5 mm pressure. 7.37 parts is obtained. VPC shows the same mixture of diastereoisomers as is obtained from the trans isomer, which mixture is free of telomers.

Analysis for $C_{11}H_8F_{15}I$

Calculated — C, 23.93; H, 1.46; F, 51.62. Found — C, 23.97; H, 1.57; F, 52.14.

EXAMPLE 6

A mixture of 50 parts of 1-iodoperfluorohexane and 0.5 parts of benzoyl peroxide in a 100 ml pear-shaped flask is heated at 90° – 95° C while ethylene is added through a gas bubbling tube at a rate just slightly faster than it reacts. After a total of 5-½ hours reaction time, absorption of ethylene ceases and VPC shows that only a small amount of the 1-iodoperfluorohexane remains. The reaction mixture is distilled at 100 mm pressure yeilding 43.7 parts of 1,1,2,2-tetrahydro-1-iodoperfluorooctane free of telomers boiling at 107° – 110° C.

Analysis for $C_8H_4F_{13}I$

Calculated — C, 20.27; H, 0.85; F, 52.11. Found — C, 20.33, H, 1.00; F, 52.04.

EXAMPLE 7

In a similar manner, 10 parts of 1-iodoperfluoroheptane and 0.2 parts of benzoyl peroxide are heated in a 25 ml flask to 90° C. Thereafter, acetylene is bubbled through the reaction mixture for about seven hours and the temperature maintained at about 95° C. 21% yield of 1,2-dihydro-1-iodoperfluoro-1-nonene by VPC is obtained, which is free of telomers.

EXAMPLE 8

The reaction procedure of Example 1 was followed except $C_8F_{17}I$ was employed as the perfluoroalkyl iodide, and azo-bis-isobutyronitrile (ABN) was employed as the catalyst with ethylene gas bubbled through the mixture. An operating temperature of 85° to 87° C was utilized. The addition product free of telomers of $C_8F_{17}CH_2CH_2I$ was obtained at a 37% yield after 10 hours.

EXAMPLE 9

The reaction procedure of Example 1 was followed except a mixture of perfluoroalkyl iodides were employed of the following composition: $C_6$ — 11.3%, $C_8$ — 24.0%, $C_{10}$ — 11.2%, $C_{12}$ — 34.5%, $C_{14}$ — 12.7%, $C_{16}$ — 4.0%, $C_{18}$ — 1.0%.

After six hours of bubbling ethylene gas, VPC showed the following percentages of starting perfluoroalkyl iodides to be present: $C_6$ — 0.2%, $C_8$ — 0.3%, $C_{10}$ — 0.3%, $C_{12}$ —, $C_{14}$ —, $C_{16}$ —, $C_{18}$ —. In contrast VPC showed $R_fCH_2CH_2I$ to be present in the following amounts $C_8$ — 9.5%, $C_{10}$ — 18.8%, $C_{10}$ — 8.3%, $C_{12}$ — 11.1%, $C_{14}$ — 32.3%, $C_{16}$ — 11.3%, $C_{18}$ — 3.3%, $C_{20}$ — 1.0%, unknown — 0.4%.

EXAMPLE 10

A pilot plant procedure was employed utilizing a conventional 10 gallon Pfaudler glasteel reactor fitted with a reflux condensor and gas inlet dip leg. A liquid mixture of $C_6F_{13}I$, $C_8F_{17}I$ and $C_{10}F_{21}I$ was charged into the reactor with a 1% by weight catalyst of benzoyl peroxide. The reactor was purged with nitrogen followed by heating of the reactor contents to 95° – 100° C, while ethylene gas was bubbled through the mixture. Since the process is exothermic, cooling was necessary to maintain the 95° – 100° C temperature. After about 2 or 3 hours, the ethylene absorption dropped off appreciably and the reaction was completed after 3 to 4 hours. Throughout the process, the gas was introduced at a slightly higher rate than it was absorbed to insure a maximum rate of reaction. VPC analysis indicated that the perfluoroalkyl iodide is at least 98% converted to the addition product by this technique. Overall yield based on theory was 97%.

EXAMPLE 11

A 25 ml pear shaped flask is fitted with thermometer gas inlet tube and dry ice condenser. The flask is charged with 10.38 parts of 1-iodoperfluorobutane and 0.2 parts of isobutyryl peroxide. Ethylene is bubbled slowly into the reaction mixture kept at 50° – 54° C for 11 hours at which time the ethylene absorption has slowed to a point indicating substantial completion of reaction. VPC discloses only 1 product peak with a small amount of unreacted 1-iodoperfluorobutane. The crude product weighs 10.7 parts; b.p. 86°/150 mm.

EXAMPLES 12 – 16

The process is repeated following the general procedure of Example 1 using stoichiometrically equivalent amounts of the following perfluoroalkyl iodides and the following olefins. The indicated addition products are obtained thereby.

| Perfluoroalkyl Iodide | Olefin | Addition Product |
|---|---|---|
| $CF_3(CF_2)_3I$ | $CH_2=CH_2CH_3$ | $CF_3(CF_2)_3CH_2\overset{CH_3}{\underset{H}{C}}-I$ |
| $(CF_3)_2CF(CF_2)_2I$ | $CH_2=CH_2$ | $(CF_3)_2CF(CF_2)_2CH_2CH_2I$ |
| $(CF_3)_2CF(CF_2)_6I$ | $CH_2=CH_2$ | $(CF_3)_2CF(CF_2)_6CH_2CH_2I$ |
| $CF_3(CF_2)_{13}I$ | $CH_2=CH_2$ | $CF_3(CF_2)_{13}CH_2CH_2I$ |

-continued

| Perfluoroalkyl Iodide | Olefin | Addition Product |
|---|---|---|
| $CF_3(CF_2)_4I$ | $CH_2=CHCH_2CH_3$ | $\begin{array}{c} H \\ | \\ CH_3(CF_2)_4CH_2C-I \\ | \\ CH_2 \\ | \\ CH_3 \end{array}$ |

EXAMPLES 17 – 20

The process was repeated following the general procedure of Example 1 employing the benzoyl peroxide catalyst and a temperature of 95° C to produce an addition product essentially free of telomers:

| Perfluoroalkyl Iodide | Olefin | Addition Product |
|---|---|---|
| $C_9F_{19}I$ | $CH_2=CH_2$ | $C_9F_{19}CH_2CH_2I$ (not characterized but reached further and product characterized) |
| $C_{11}F_{23}I$ | $CH_2=CH_2$ | $C_{11}F_{23}CH_2CH_2I$ (not characterized but reacted further and product characterized) |
| $C_7F_{15}I$ | $CH_3C\equiv CH$ | $\begin{array}{c} CH_3 \\ | \\ C_7F_{15}CH=C-I \end{array}$ bp. 78–79/14 mm cis, trans isomers |
| $C_7F_{15}I$ | $CH_3C\equiv CCH_3$ | $\begin{array}{c} CH_3 \quad CH_3 \\ | \quad\quad | \\ C_7F_{15}C=C-I \end{array}$ bp. 79–81/10 mm cis, trans isomers |

EXAMPLE 21

A mixture of 9.08 parts of 1,4-diiodo-perfluorobutane and 0.1 part of benzoyl peroxide in a 15 ml. pear-shaped flask, fitted with condenser, thermometer and gas inlet tube was heated to 90° C. Ethylene is bubbled into the mixture at a rate slightly faster than it reacts, keeping the temperature at 90°–95° C. The reaction is followed by checking the reaction mixture by VPC. After 3 hours, the reaction mixture contains 40% unreacted 1,4-diiodo-perfluorobutane, 40% of the 1:1 adduct 1,6-diiodo-5,5,6,6-tetrahydroperfluorohexane and 20% of the 1:2 adduct 1,8-diiodo-1,1,2,2,7,7,8,8-octa-hydroperfluorooctane. After a total of 23 hours of reaction, VPC shows only the 1:2 adduct along with two trace impurities. No evidence of any telomers is observed. The product, after purification by recrystallization from 60 parts heptane, weighs 5.9 parts and melts 89°–92°.

Analysis for $C_8H_8F_8I_2$

Calculated — C, 18.84; H, 1.58; F, 29.80; I, 49.77.
Found — C, 19.25; H, 1.83; F, 29.94; I, 48.37.

While the invention has been explained by detailed description of certain specific embodiments, it is understood that various modifications and substitutions can be made in any of them within the scope of the appended claims which are intended also to include equivalents of such embodiments. For example to illustrate obvious modifications falling within the scope of the disclosure of the present invention, mixtures of the disclosed perfluoroalkyl iodides as well as mixtures of olefins and acetylenes may be employed as starting materials.

What is claimed is:

1. A process for the addition of perfluoroalkyl iodides of the formula $ZC_nF_{2n}I$, where Z represents F or I, n is an integer of 4 – 18, said iodides are liquid at reaction temperature, to non-halogenated olefins or non-halogenated acetylenes which are gaseous at the employed reaction temperature, which comprises bubbling said olefin or acetylene into said liquid iodide, in the presence of a free-radical generating catalyst, at atmospheric or less than atmospheric pressure, at a reaction temperature of about 40° C to about 220° C, and recovering the reaction addition product which is essentially free of telomers.

2. A process for the addition of perfluoroalkyl iodides of the formula $ZC_nF_{2n}I$, where Z represents F or I, n is an integer of 4 – 18, said iodides are liquid at reaction temperature, to non-halgenated olefins or non-halogenated acetylenes which are gaseous at the employed reaction temperature, which comprises bubbling said olefin or acetylene into said liquid iodide, said liquid iodide containing a catalystic amount of a free-radical generating catalyst, at atmospheric or less than atmospheric pressure, at a reaction temperature of about 40° to about 220° C, and recovering the then formed reaction addition product which is essentially free of telomers.

3. The process of claim 2 wherein said temperature is between 50° and 220° C.

4. The process of claim 3 where said temperature is below 100° C.

5. The process of claim 3 where n is an integer of 6 to 10.

6. The process of claim 1 where n is an integer of 6 to 10.

7. The process of claim 2 wherein an olefin is employed and Z represents F wherein the addition product is of the formula:

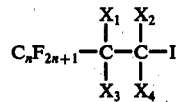

wherein $X_1$, $X_2$, $X_3$ and $X_4$ represents hydrogen or an alkyl of 1 to 4 carbon atoms with the combinations of $X_1$, $X_2$, $X_3$ and $X_4$ representing not more than two alkyl groups.

8. The process of claim 7 wherein said alkyl is methyl or ethyl.

9. The process of claim 7 wherein said temperature is below 100° C.

10. The process of claim 8 wherein said temperature is below 100° C.

11. The process of claim 2 wherein acetylene is employed and Z represents F wherein the addition product is of the formula:

$$C_nF_{2n+1}CX_1 = CX_2I$$

wherein $X_1$ and $X_2$ represents hydrogen or an alkyl of 1 to 4 carbon atoms.

12. The process of claim 11 wherein said alkyl represents methyl or ethyl.

13. The process of claiim 2 whrein Z represents I and the ratio of perfluoroalkyl iodide to said olefin or acetylene in the addition product is 1:2.

14. A process for making 1,1,2,2-tetrahydro-1-iodoper-fluoroheptane comprising bubbling ethylene into liquid 1-iodoper-fluoroheptane at atmospheric or less than atmospheric pressure, at a reaction temperature of about 50° C to about 220° C in the presence of a free-radical generating catalyst, and recovering the reaction addition product 1,1,2,2-tetrahydro-1-iodoperfluorononane, which is essentially free of telomers.

* * * * *